(12) United States Patent
Hauri et al.

(10) Patent No.: US 9,782,249 B2
(45) Date of Patent: Oct. 10, 2017

(54) LIGAMENT-TENSIONING DEVICE AND METHOD

(71) Applicant: Smith and Nephew Orthopaedics AG, Rotkreuz (CH)

(72) Inventors: Thomas Hauri, Staffelbach (CH); Jan Stifter, Unterehrendingen (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 1 day.

(21) Appl. No.: 14/967,976

(22) Filed: Dec. 14, 2015

(65) Prior Publication Data

US 2016/0095694 A1 Apr. 7, 2016

Related U.S. Application Data

(62) Division of application No. 12/090,850, filed as application No. PCT/EP2006/010052 on Oct. 18, 2006, now Pat. No. 9,216,097.

(30) Foreign Application Priority Data

Oct. 18, 2005 (DE) ........................ 10 2005 049 851

(51) Int. Cl.
*A61F 2/38* (2006.01)
*A61F 2/08* (2006.01)
(Continued)

(52) U.S. Cl.
CPC .......... *A61F 2/0811* (2013.01); *A61B 17/025* (2013.01); *A61F 2/0805* (2013.01);
(Continued)

(58) Field of Classification Search
CPC .............. A61B 17/025; A61B 17/0268; A61B 2017/0268; A61B 2017/681
See application file for complete search history.

(56) References Cited

U.S. PATENT DOCUMENTS

| | | |
|---|---|---|
| 4,501,266 A | 2/1985 | McDaniel |
| 4,997,432 A | 3/1991 | Keller |

(Continued)

FOREIGN PATENT DOCUMENTS

| | | | |
|---|---|---|---|
| DE | 2253929 A1 | 5/1973 | |
| DE | 3809793 A1 | 10/1989 | |

(Continued)

OTHER PUBLICATIONS

International Search Report for related PCT Application No. PCT/EP2006/010052, mailed Apr. 12, 2007, 11 pages.

(Continued)

*Primary Examiner* — Matthew Lawson
(74) *Attorney, Agent, or Firm* — Taft Stettinius & Hollister LLP (57) ABSTRACT

A ligament-tensioning device and method for activation of the ligament and/or capsule system in the implantation of a joint implant. The device includes a distal bearing plate for bearing against a distal skeletal part, and also includes first and second proximal bearing plates, each of which partially overlaps the distal bearing plate in a first in-use position, for bearing against a proximal skeletal part. The device further includes means for relative displacement of the proximal bearing plates to increase their spacing from the distal bearing plate. The displacement means includes a scissor-type guide means that supports the respective proximal bearing plate in the ventral-dorsal as well as the medial-lateral parallel position with respect to the distal bearing plate.

27 Claims, 7 Drawing Sheets

(51) Int. Cl.
*A61B 17/02* (2006.01)
*A61F 2/46* (2006.01)

(52) U.S. Cl.
CPC .... *A61F 2/4657* (2013.01); *A61B 2017/0268* (2013.01); *A61F 2/38* (2013.01); *A61F 2/4684* (2013.01); *A61F 2002/4624* (2013.01); *A61F 2002/4661* (2013.01)

(56) References Cited

U.S. PATENT DOCUMENTS

| | | | |
|---|---|---|---|
| 5,540,696 | A | 7/1996 | Booth et al. |
| 6,056,756 | A | 5/2000 | Eng et al. |
| 6,251,067 | B1 | 6/2001 | Strickholm |
| 7,309,357 | B2 | 12/2007 | Kim |
| 2003/0069644 | A1 | 4/2003 | Kovacevic et al. |
| 2004/0097951 | A1 | 5/2004 | Steffensmeier |
| 2005/0020941 | A1* | 1/2005 | Tarabichi ............. A61B 5/1071 600/587 |
| 2005/0177170 | A1* | 8/2005 | Fisher ................... A61B 17/02 606/88 |
| 2006/0111790 | A1* | 5/2006 | Dietz .................... A61F 2/4657 623/20.32 |
| 2006/0149277 | A1* | 7/2006 | Cinquin ............... A61B 17/025 606/90 |
| 2008/0091209 | A1 | 4/2008 | Schmotzer et al. |

FOREIGN PATENT DOCUMENTS

| | | |
|---|---|---|
| DE | 20320501 U1 | 12/2004 |
| DE | 10348585 A1 | 4/2005 |
| GB | 1386828 A | 3/1975 |
| WO | 0078255 A1 | 12/2000 |
| WO | 2004078047 A1 | 9/2004 |

OTHER PUBLICATIONS

English Translation of International Preliminary Report on Patentability for related PCT Application No. PCT/EP2006/010052, mailed Apr. 29, 2008, 12 pages.

* cited by examiner

LIGAMENT-TENSIONING DEVICE AND METHOD

CROSS REFERENCE TO RELATED APPLICATIONS

This application is a divisional of U.S. patent application Ser. No. 12/090,850 filed Oct. 22, 2008, which is a U.S. national stage application of International Application No. PCT/EP2006/010052 filed Oct. 18, 2006, which claims priority to German Patent Application No. 10 2005 049 851.5 filed Oct. 18, 2005, the contents of each application hereby incorporated herein by reference in its entirety.

TECHNICAL FIELD

The invention relates to a ligament-tensioning device and method for activation of the ligament and/or capsule system in the implantation of a joint implant.

BACKGROUND

Other ligament-tensioning devices having a similar function are known. For example, International Publication No. WO 00/78225 A1 discloses a ligament-tensioning device which, in addition to having a prismatic, cylindrical or plate-shaped base body, which has a bearing surface for bearing against a first bone adjoining a non-spherical joint, has right and left tensioning levers having second bearing surfaces which are to be applied to the joint-side surface of a second bone adjoining the joint, the operation of associated handgrips and operating levers being coordinated. The opposing portions (bearing surfaces) are supported with respect to one another by four-bar lever mechanisms.

DE 103 48 585 A1 discloses a further ligament-tensioning device which comprises a first, distal bearing plate for bearing against a first skeletal part and a second, proximal bearing plate for bearing against a second skeletal part, the two bearing plates being displaceable relative to one another by a hydraulic drive means and, especially, being tiltable relative to one another by means of a central axis. In addition, they are joined to one another by means of a base body, the distal bearing plate in particular being joined rigidly thereto.

WO 2004/078047 A1 discloses a further ligament-tensioning device which comprises a distal bearing plate and two proximal bearing plates independently guided and displaceable relative thereto. Guidance is affected therein in each case by means of a double hinge connection and the drive is preferably likewise affected hydraulically.

According to current experiences, the known ligament-tensioning devices still have certain disadvantages in use. Those disadvantages relate especially to the desired exact alignment between the opposing bearing plates and to the expense associated with a hydraulic drive device. In addition, when the known ligament-tensioning devices are used, the joint in question has to be kept open, because substantial parts of the device protrude.

Embodiments of the invention therefore address the problem of providing an improved ligament-tensioning device having a wide variety of possible applications that is economical and reliably satisfies the requirements of practice.

SUMMARY

Some embodiments of the invention can further provide a ligament-tensioning device that is fully insertable into the joint in question, thus making it possible to close the joint capsule again after insertion. For that purpose, in particular the bearing plates are to be dimensioned to match the joint in question such as, for example, a knee joint, and projecting parts (such as, for example, handgrips/levers or hydraulic lines which project in the prior art) are generally to be avoided. In that respect, some embodiments of the invention can include the concept of providing a purely internal drive means or internal displacement means for the relative displacement of the opposing bearing plates.

In one embodiment, the invention provides parallel guidance between the distal bearing plate and the proximal bearing plates that is precise in both the ventral-dorsal and the medial-lateral directions. This can be realized advantageously by a suitable guide means in accordance with the scissors principle. Other two-plane parallel guide means also can be used, however, including the use of two hinge joints that are not axially parallel to one another (especially enclosing an angle of 90° with respect to one another).

In further embodiments, the invention can also include the concept of providing, as drive means for pushing the distal bearing plate and the proximal bearing plates apart from one another, a separate drive element in each case, that drive element being, moreover, a drive element that functions without auxiliary energy. In these embodiments, the invention can assign to each proximal bearing plate a spring element which, in a starting state in which the proximal bearing plate is spaced a minimum distance apart from the distal bearing plate, can store the drive energy and release it for the purpose of increasing the spacing when the ligament-tensioner is brought into operation. In a further embodiment, the invention can also include the concept of assigning to that spring element or to the opposing bearing plates a locking means for releasable fixing in the starting position.

In principle, however, a drive means having auxiliary energy, for example an electromotive, electromagnetic, hydraulic or pneumatic drive means, also comes into consideration. Such a drive means can drive both proximal bearing plates jointly, it being possible for the bearing plates to take up different end positions in force equilibrium with the surrounding capsule/ligament structure. The said drive means can, however, also be provided separately for each proximal bearing plate.

It should be noted that the terms "distal bearing plate" and "proximal bearing plate" are used herein with reference to preferred in-use positions of the ligament-tensioner, for example when used in the knee. For that application, it is also possible to speak synonymously of a tibia bearing plate and a femur bearing plate, respectively. The invention is also to be understood, however, as possibly including transpositions of the bearing plates in respect of their position further from or closer to the center of the body (distal or proximal, respectively).

In further embodiments, the spring element can have a compression spring element arranged in a region of overlap between the proximal and distal bearing plates and supported against both, the spring element having, for example, a steel or titanium helical spring having a suitable spring characteristic. The spring can have a spring constant matched to a predetermined tensioning force in order to provide, for example, a tensioning force that is substantially constant over its travel in the range between 50 and 90 N, especially 70 N.

To realize a relatively high and constant tensioning force and to also realize a small initial height of the spring element in the tensioned state, the device can use special forms of the compression springs tailored thereto. In one embodiment, the steel or titanium helical spring for increasing the travel is of conical or double-cone form, and has a pitch indirectly proportional to the local winding diameter. The conical shape of the spring element can be chosen so that the overall height in the tensioned state is substantially less than that of a comparable helical spring having a cylindrical basic shape.

In an alternative embodiment, the spring element can have a flexural spring element, and more specifically, for example, a steel spiral or leaf spring.

The scissor-type guide means can have two scissor joints arranged close to opposite ends of the proximal bearing plate, that is to say spaced as far apart from one another as possible. In various embodiments, it is possible for those scissor joints to be arranged in the ventral-dorsal direction (one behind the other) or in the medial-lateral direction (one next to the other). In one embodiment of the scissor-type guide means, the ends of the scissor joints can be inserted in grooves in the distal and proximal bearing plates and a limb or an end of each of the two limbs is rotatably fixed therein by means of bearing pins extending perpendicular to the run of the groove.

Additionally, improved guidance and fixing to one another of the opposing bearing plates may be obtained by providing at each end of the free limb, or at the free end of each of the two limbs, a slide peg for guiding the respective limb or end in a groove formed to match the slide peg. To increase the rigidity and to provide even better guidance, the scissor joints may also be joined to one another by means of at least one connecting rod mounted at the end of a limb of each scissor joint.

For adaptation to the specific anatomical conditions of different patients, the first and second proximal bearing plates each comprise an upper and a lower part, the lower part being provided with means for mounting the spring element and the scissor-type guide means, and the upper part being fixed releasably on the lower part to increase the thickness of the bearing plate in question. The ligament-tensioning device can be used with a set of upper parts of different thicknesses to provide a solution to the mentioned adaptation problem.

The above-mentioned locking is released by the provision on the distal bearing plate, or the first and second proximal bearing plates, of releasable locking means for independent locking of the first and second proximal bearing plates to the distal bearing plate at a minimum spacing and with a maximum spring tension with respect thereto.

In some embodiments, the locking means each have a hook pivotally mounted on the respective bearing plate and engaging in the opposing bearing plate, on which hook there is provided a first tool-engagement portion for actuation. The tool-engagement portion is preferably configured for engagement of a hex key tool, for example a 3.5 mm hex key.

In one embodiment of the locking means having a pivotable hook, an engagement portion for that hook is formed in the material of the first and second proximal bearing plates in spatial association with the hook articulated on the distal bearing plate.

In an additional embodiment, a first bearing peg of a scissor joint of the first and second proximal bearing plates can project beyond the outer edge thereof and be so arranged relative to the hook pivotally mounted on the distal bearing plate so that it forms a counter-bearing of the locking means. In that embodiment, or alternatively independently thereof, a second bearing peg of a scissor joint of the first and second proximal bearing plates projects beyond the outer edge thereof and is so arranged relative to the hook pivotally mounted on the distal bearing plate so that it forms the hinge pin thereof.

On account of high forces, a tool is used for positioning the ligament tensioner at the site of use, and a second tool-engagement portion, such as a cylindrical recess, is provided on the side edges of the distal bearing plate and of first and second proximal bearing plates for engagement of a positioning tool. The provision of a separate tool is advantageous with a view to realizing a ligament tensioner that can be fully integrated into a joint.

A further embodiment provides a construction for the releasable coupling-on of a sizer, which couples the proximal and distal skeletal parts in flexion to facilitate axial transmission from the one skeletal part to the other, taking account of the ligament tension. In principle, the coupling-on includes simply being in contact with suitably prepared bearing surfaces, but it also includes connecting means for fixing the sizer on the distal bearing plate. In some embodiments, the connecting means can comprise two clip-like extensions on the distal bearing plate which, each engaging around a side edge of the proximal bearing plates, run to a base plate of the sizer.

Arrangements comprising the proposed ligament-tensioning device and a matching positioning tool and/or a sizer matched thereto are also to be regarded as being included in the scope of protection.

BRIEF DESCRIPTION OF THE DRAWINGS

Advantages and functional features of the invention will otherwise be found in the following description with reference to the Figures.

DETAILED DESCRIPTION OF THE EMBODIMENTS

Figure 1:
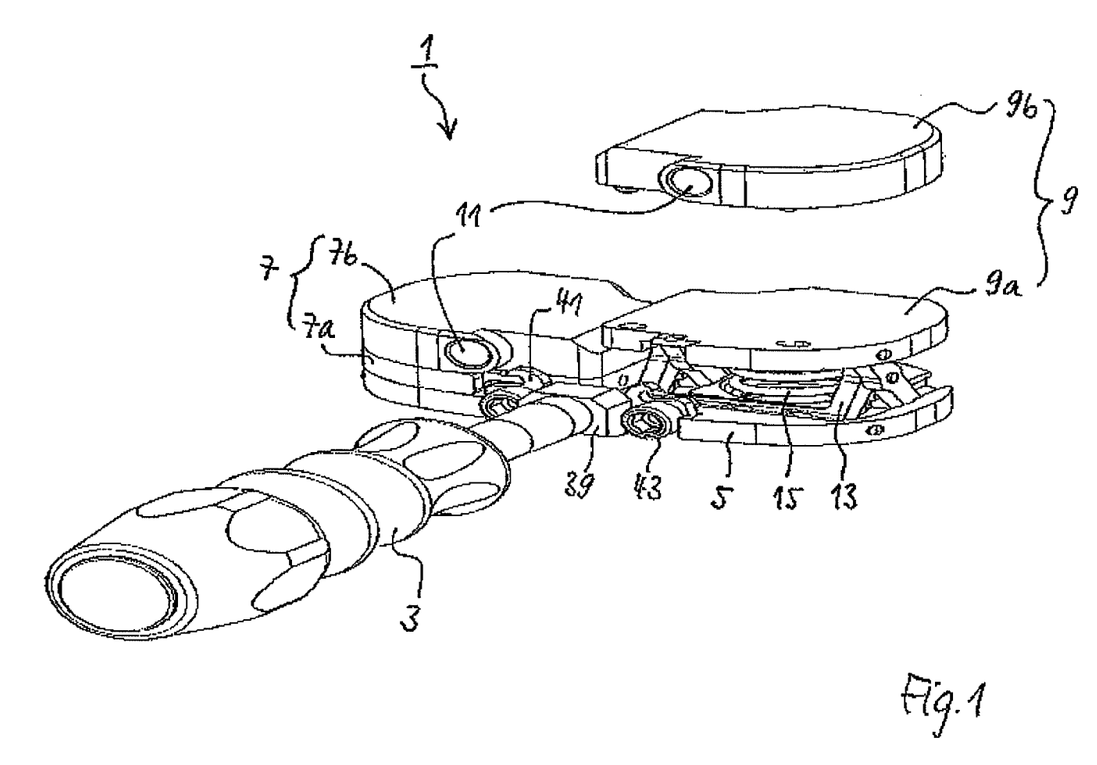
FIG. 1 is a perspective view of a ligament-tensioning device according to one embodiment of the invention ventrally obliquely from above, partly as an exploded view, with an attached positioning tool.

FIGS. 1-4 show various views of an embodiment of a ligament-tensioning device 1 in various states (described below), with FIG. 1 showing the device co-operating with a positioning tool.

Figure 2:
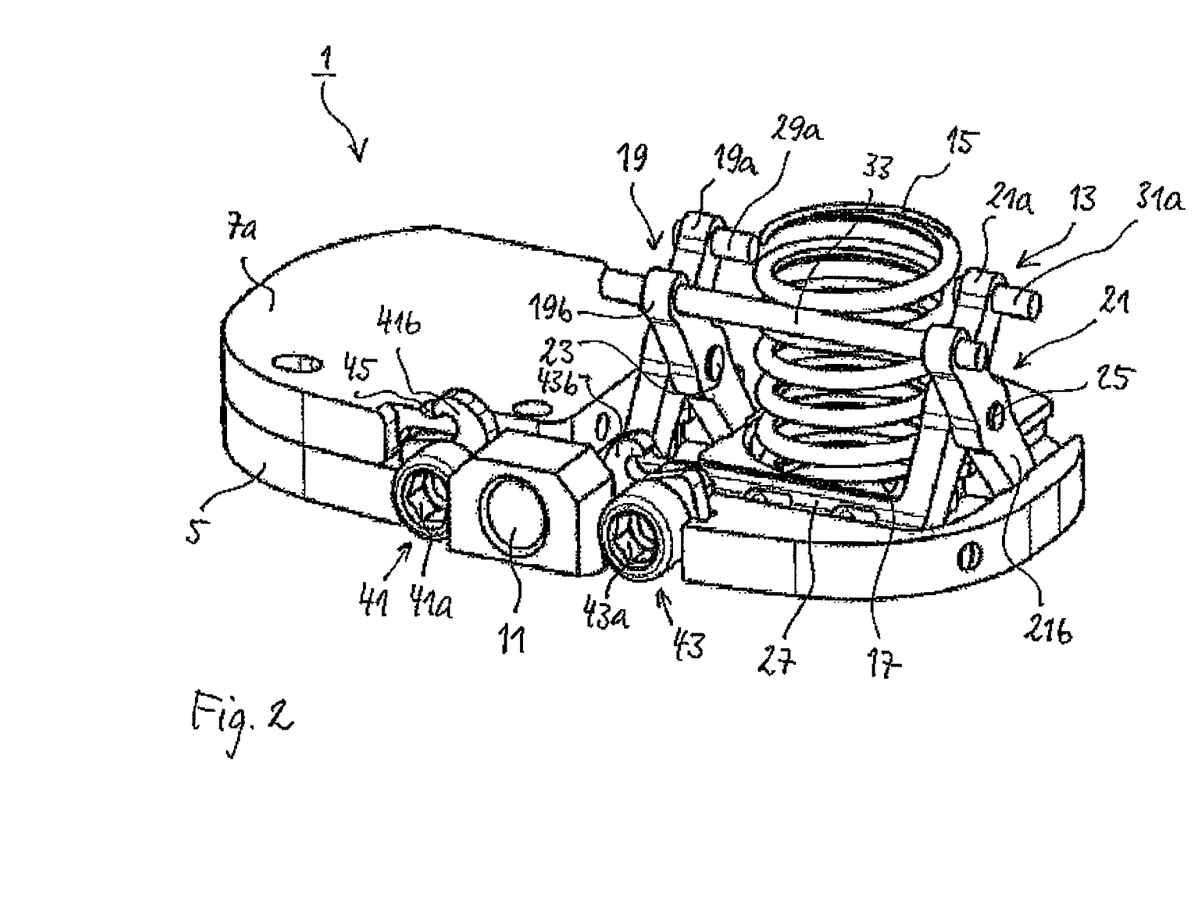
FIG. 2 is a perspective view of the ligament-tensioning device according to FIG. 1 ventrally obliquely from above, with the second proximal bearing plate removed and the associated displacement means in the fully extended state.

The ligament-tensioning device 1 comprises a distal bearing plate 5, which is approximately kidney-shaped in plan view, and, arranged in parallel therewith and opposite thereto, two proximal bearing plates 7 and 9 each of which overlaps approximately half of the distal bearing plate, the proximal bearing plates each comprising a lower part 7a, 9a and an upper part 7b, 9b. For positioning the ligament-tensioning device 1 with the aid of the positioning tool 3 there are provided on the front side edges of the distal and proximal bearing plates respective cylindrical recesses 11 as engagement portions (FIG. 1 shows the recesses in the proximal bearing plates, more specifically in the upper parts 7b, 9b thereof, while FIG. 2 shows the central recess 11 in the distal bearing plate 5).

The proximal bearing plates 7 and 9 (or, more specifically, the lower parts 7a, 9a thereof) are joined to the illustrated device 1 by means of a scissor-type guide means 13 and are tensioned against the device by a steel compression spring 15 as spring element. As can be seen most clearly in FIGS. 2 and 3, the helical spring 15 is seated in a matching circular recess 17 on the upper side of the distal bearing plate 5, and a similar mounting (not shown) is provided on the underside of the respective associated proximal bearing plate.

The scissor-type guide means 13 comprises medial and lateral scissor joints 19, 21 which each comprise two limbs 19a, 19b and 21a, 21b pivotally connected by means of a hinge pin 23, 25, respectively. The limbs 19a, 21a are joined to one another at one end by means of an integrally formed bridge or connecting bar 27, while a slide peg or pin 29a, 31a is inserted in their other end for connection to the lower part 9a (omitted in FIGS. 2 and 3) of the second bearing plate. In a similar way, one end of each of the limbs 19b, 21b can be joined by means of a connecting rod 33 inserted perpendicular to the plane of extension, which rod projects beyond the medial or lateral outer side of the respective limb and forms further slide pegs (not shown separately) thereon.

Figure 3:
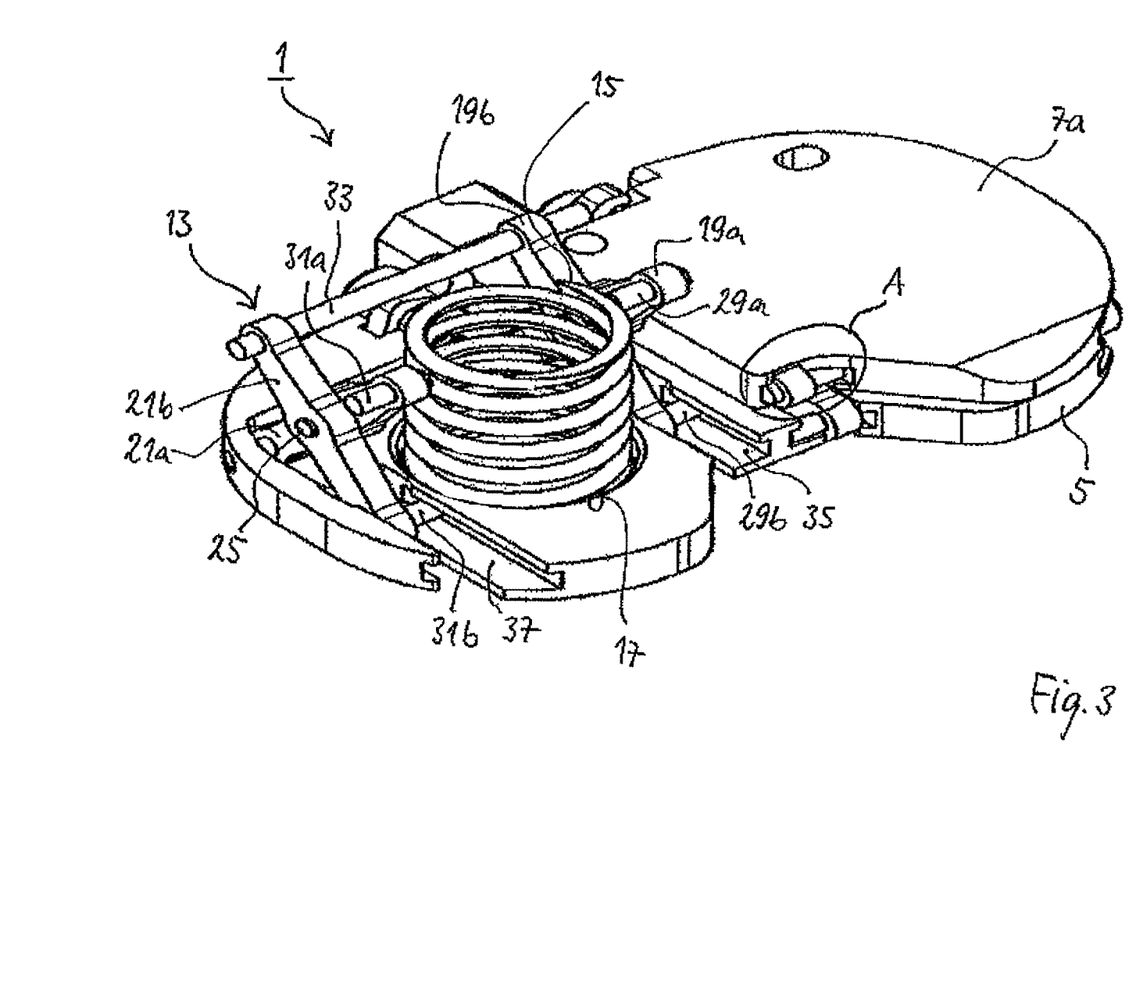
FIG. 3 is a perspective view of the ligament-tensioning device according to FIG. 1, with the second proximal bearing plate removed and the displacement means in an intermediate position, dorsally obliquely from above.
Figure 4:
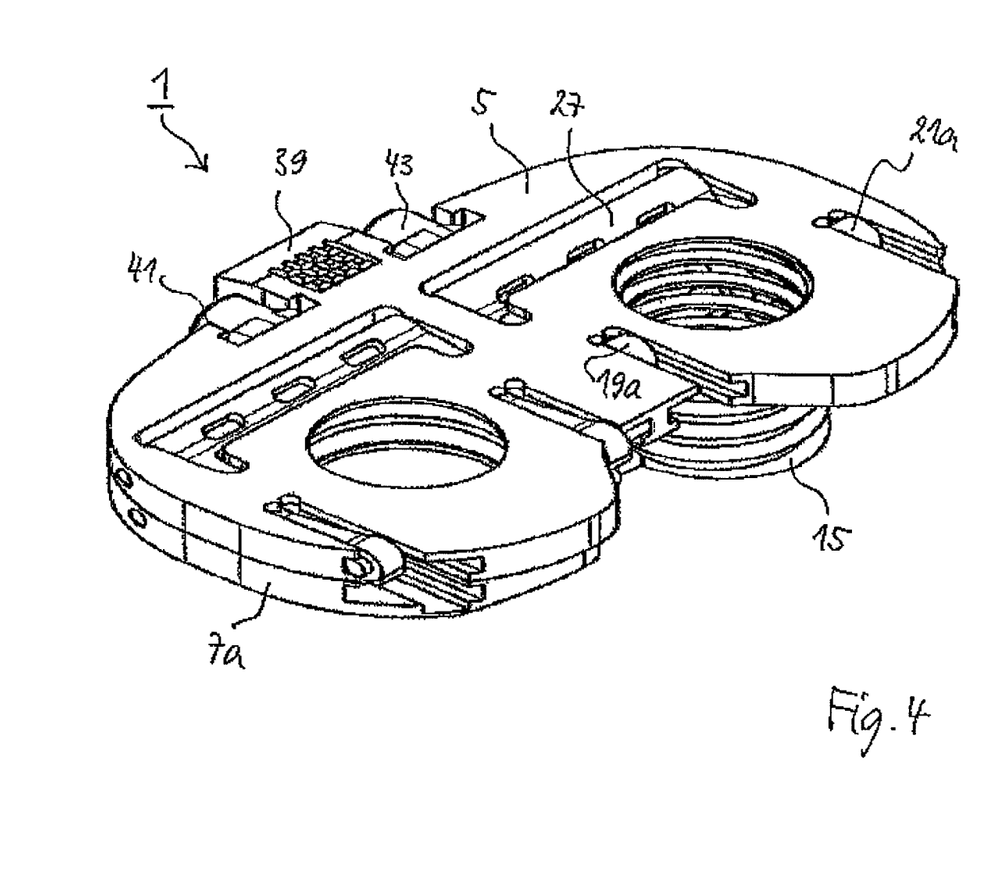
FIG. 4 is a perspective view of the ligament-tensioning device according to FIG. 1, with the second proximal bearing plate removed, ventrally obliquely from below.

The opposite ends of the limbs 19b, 21b are in turn each provided with a separate slide pin 29b, 31b, respectively. Those slide pegs 29b, 31b engage (as can be seen most clearly in FIG. 3) in correspondingly dimensioned grooves 35, 37 in the distal bearing plate 5 which, in the in-use position of the ligament-tensioning device, run dorsally-ventrally and fix the scissor-type guide means so as to be slidable therewith in the distal bearing plate 5. (As can be seen to some extent in the portion of FIG. 3 showing the lower part 7a of the first proximal bearing plate 7 (see detail "A"), a corresponding groove structure, which does not have a separate reference numeral herein, is provided in the proximal bearing plates).

As can be seen most clearly in FIG. 2, on the ventral side edge (front edge) of the distal bearing plate 5, on both sides of an extension containing the cylindrical recess 11 there are mounted two pivotable hook elements 41, 43, each of which comprises a hex key engagement portion 41a, 43a and an integrally formed hook portion 41b, 43b, respectively. As can be seen in FIG. 2 in the region of the first proximal bearing plate, the hook portions engage in a recess on the upper side of the respective bearing plate lower part, which recess is shaped to correspond to the shape of the hook, with only the recess 45 in the lower part 7a of the first proximal bearing plate being shown in FIG. 2. By means of such engagement, the proximal bearing plates are held at a minimum distance from the distal bearing plate. By rotation of the respective hook element 41, 43 with a suitable tool, that locking is released and the proximal bearing plate in question can be moved away from the distal bearing plate under the bias of the associated compression spring 15 until its movement comes to a standstill in force equilibrium with the capsule/ligament tension acting at the site of use.

Figure 5:
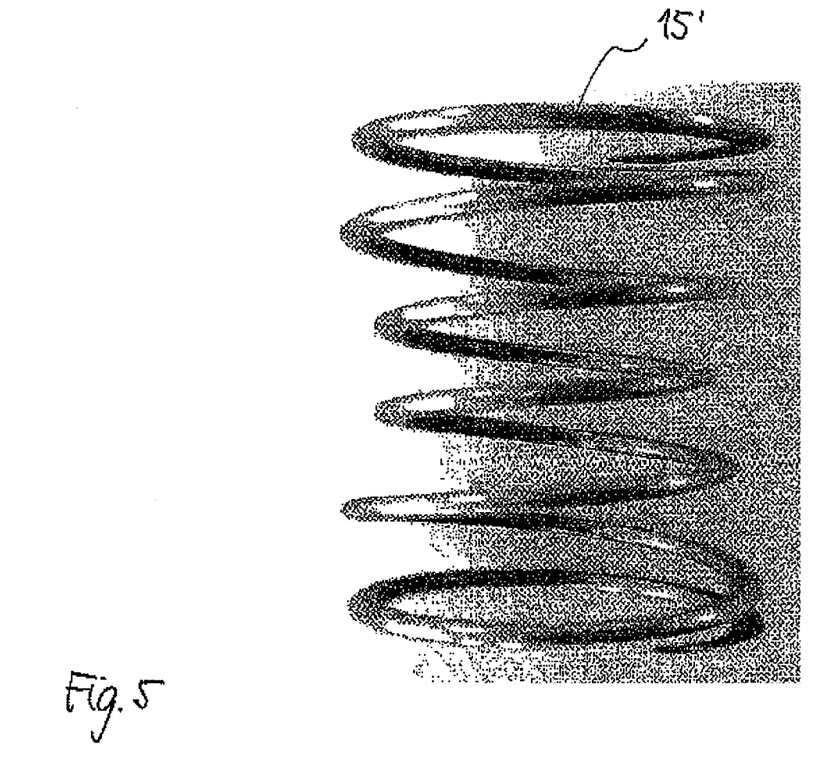
FIG. 5 is a perspective view of a helical spring suitable for use as spring element in the ligament-tensioning device according to FIG. 1, as shown with a double-cone configuration.
Figure 6A:
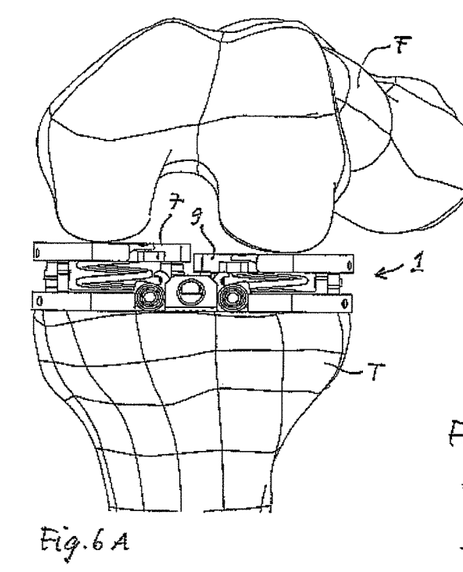
FIG. 6A-6D show various views of the ligament-tensioning device according to FIG. 1 in its in-use state installed in a knee joint.
Figure 6B:
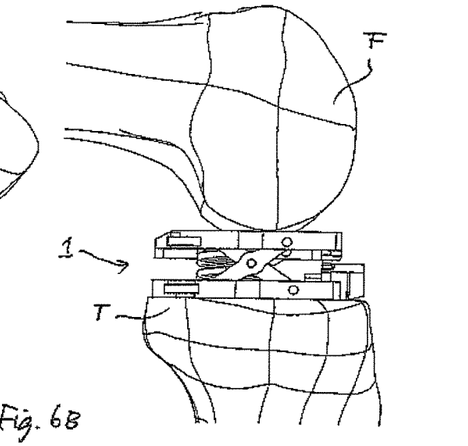
Figure 6C:
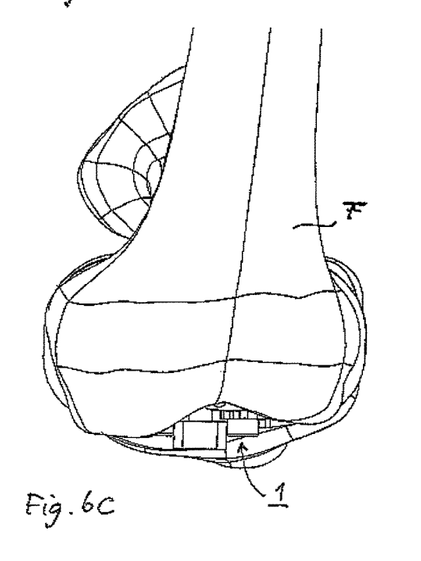
Figure 6D:
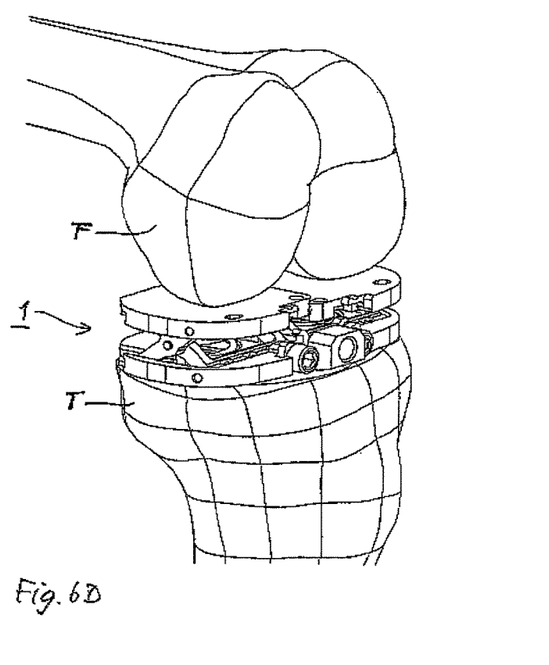
Figure 7A:
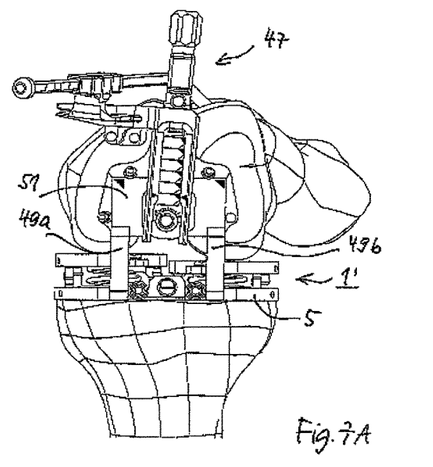
FIG. 7A-7D show various views of the ligament-tensioning device according to FIG. 1 in its in-use state installed in a knee joint, with a coupled-on sizer.
Figure 7B:
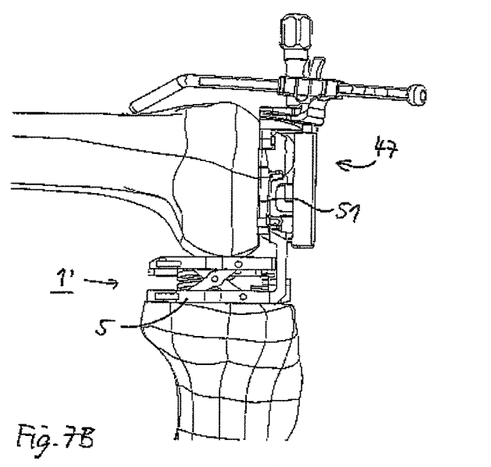
Figure 7C:
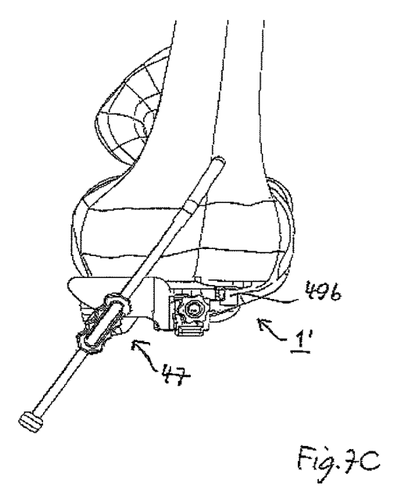
Figure 7D:
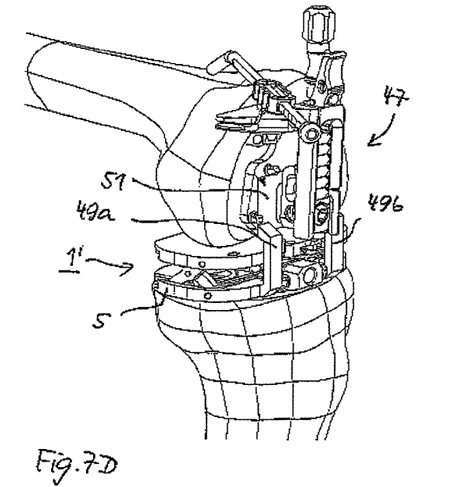

Whereas in FIGS. 1-4 a cylindrical helical spring 15 is shown as the spring element, FIG. 5 shows, as a modification, a double-cone helical spring 15' which, by virtue of its lesser overall height in the tensioned state, can be used preferably in the ligament-tensioning device 1 according to FIGS. 1-4, it being possible (in a configuration not shown) for the pitch of the winding in the lower and upper regions of greater diameter to be smaller than in the central region, in order that a trouble-free spring action is realized over the entire travel.

The above-described ligament-tensioning device 1 is constructed for use in a knee joint and is shown in that in-use state in various views in FIGS. 6A to 6D. The Figures clearly show the matching of the dimensions, especially the length/width ratio, and the configuration of the two proximal bearing plates 7, 9 to the anatomical conditions of the knee joint and the overall dimensions and relative sizes of the tibia T and the (resected) femur F. As shown, the device can have a length:width ratio of approximately 3:2 in accordance with that of a proximal tibia.

FIGS. 7A to 7D show a diagrammatic view, comparable to FIG. 6A-6D, of a modified configuration of a ligament-tensioning device 1' with a coupled-on sizer 47. A sizer serves for the intra-operative coupling of tibia and femur in flexion so that axis transmission of the tibial axis, taking account of the ligament tension, to the femur can be effected. It is accordingly possible to define the optimum size and position of a knee implant in the ventral-dorsal direction and in rotation. Attention should be drawn to the provision of connecting means between the ligament-tensioning device 1' and the sizer 47, namely two clip-like extensions or connecting bars 49a, 49b on the distal bearing plate 5, which engage over the proximal bearing plates (not shown) at one side edge thereof and make a connection to a base plate 51 of the sizer 47.

The implementation of the invention is not confined to the embodiments described herein and the last-mentioned modification of the spring element, but is also possible in a multiplicity of embodiments which lie within the scope of the invention. For example, in some embodiments, a scissor-type guide means may be turned through 90° with respect to the embodiment shown, and in which some of the slide pegs or pins can be constructed simultaneously as bearing pins for the fixed positioning of a limb end in the associated bearing plate. In such embodiments, it is also possible for such a bearing pin to be used simultaneously as hinge pin of the pivotable locking hooks. Furthermore, in the case of the proximal bearing plates it is also possible for the upper parts to be omitted, and numerous degrees of freedom exist in respect of the exact shape and relative dimensions of the bearing plates.

LIST OF REFERENCE NUMERALS 1 ligament-tensioning device
2 positioning tool
5 distal bearing plate
7, 9 proximal bearing plates
7a, 9a lower parts of the proximal bearing plates
7b, 9b upper parts of the proximal bearing plates
11 cylindrical recess
13 scissor-type guide means
15 cylindrical helical spring
15' double-cone helical spring
17 circular recess 19 medial scissor joint
19a, 19b limbs of the medial scissor joint
21 lateral scissor joint
21a, 21b limbs of the lateral scissor joint
23 hinge pin of the medial scissor joint
25 hinge pin of the lateral scissor joint
27 connecting bar
29a, 29b, 31a, 31b slide pegs
35, 37 grooves
41, 43 hook elements
41a, 43a hex key engagement portions
41b, 43b integral hook portions
45 recess
47 sizer
49a, 49b extensions
51 base plate

What is claimed is:

1. A method of putting a ligament in tension, comprising:
resecting a joint surface of at least one of a tibia and a femur;
inserting a ligament-tensioning device having at least one distal bearing plate and at least one proximal bearing plate into a space between the tibia and femur, the device inserted in a first compact configuration, at least one of the plates disposed adjacent to the resected joint surface, the device having at least one displacer for displacing the proximal and distal bearing plates away from one another, wherein the displacer is accommodated within the space between the tibia and femur such that a joint capsule connecting the tibia and femur can be closed while the device including the displacer is positioned in the joint capsule;
displacing the at least one proximal bearing plate away from the at least one distal bearing plate via the displacer so as to move the device into a second expanded configuration to increase a space between the tibia and the femur; and
closing the joint capsule connecting the tibia and femur to enclose the device including the displacer entirely within the joint capsule.

2. The method of claim 1, wherein the joint capsule is closed prior to displacing the at least one proximal bearing plate away from the at least one distal bearing plate.

3. The method of claim 2, wherein prior to the closing step, a sizer is releasably attached to a distal bearing plate after being inserted between the femur and tibia and configured to define a preferable size for the at least one proximal bearing plate.

4. The method of claim 1, wherein the displacer comprises a self-contained unit that does not require auxiliary energy to displace the proximal and distal bearing plates away from one another.

5. The method of claim 4, wherein the at least one displacer comprises a spring element.

6. The method of claim 4, further comprising actuating the at least one displacer.

7. The method of claim 4, wherein the at least one displacer comprises a plurality of displacers that can be activated independently.

8. The method of claim 4, wherein the at least one displacer is activated by the interaction of a hex key and an engagement portion of at least one bearing plate.

9. The method of claim 1, wherein the step of displacing comprises mechanically displacing.

10. The method of claim 1, wherein the resecting comprises resecting both the femur and the tibia.

11. The method of claim 1, wherein the plates are positioned by a positioning tool that engages a cylindrical recess on at least one of the side edges of the at least one distal bearing plate and the at least one proximal bearing plate.

12. A method of putting a ligament in tension, comprising:
resecting a joint surface of at least one of a tibia and a femur;
inserting a ligament-tensioning device into a space between the tibia and the femur, the device having at least one distal bearing plate and at least one proximal bearing plate, the device inserted into the space in a first compact configuration, and with at least one of the distal and proximal bearing plates disposed adjacent to the resected joint surface, the device having a displacer for displacing the proximal and distal bearing plates away from one another, wherein the displacer is accommodated within the space between the tibia and femur such that a joint capsule connecting the tibia and femur can be closed while the device including the displacer is positioned in the joint capsule;
displacing the at least one proximal bearing plate and the at least one distal bearing plate away from one another via the displacer so as to transition the device into a second expanded configuration to increase a space between the tibia and the femur; and
closing the joint capsule connecting the tibia and femur to enclose the device including the displacer entirely within the joint capsule.

13. The method of claim 12, wherein the at least one proximal bearing plate includes first and second proximal bearing plates, each of which at least partially overlapping the distal bearing plate.

14. The method of claim 12, wherein the device further comprises:
at least one releasable locking device structured to selectively lock the distal bearing plate relative to the proximal bearing plate; the method further comprising:
engaging the releasable locking device with both the distal bearing plate and the proximal bearing plate to maintain an initial distance between the distal and proximal bearing plates; and
disengaging the releasable locking device from one of the distal bearing plate and the proximal bearing plate to permit relative displacement of the proximal bearing plates away from the distal bearing plate to an increased distance between the distal and proximal bearing plates.

15. The method of claim 12, wherein the at least one proximal bearing plate includes first and second proximal bearing plates, each of which at least partially overlapping the distal bearing plate;
wherein the distal bearing plate or the first and second proximal bearing plates comprise releasable locking devices for independent locking of the first and second proximal bearing plates to the distal bearing plate at a minimum spacing;
wherein the releasable locking devices each have a first position that is engaged with both the distal bearing plate and a corresponding one of the first and second proximal bearing plates to maintain the minimum spacing;
wherein the releasable locking devices each have a second position that is disengaged from one of the distal bearing plate and the corresponding one of the first and second proximal bearing plates to permit relative displacement of the corresponding one of the first and second proximal bearing plates away from the distal bearing plate to an increased spacing.

16. The method of claim 15, wherein the releasable locking devices are each pivotally mounted to one of the distal bearing plate and the corresponding one of the first and second proximal bearing plates and pivot between the first and second positions.

17. The method of claim 12, wherein the device further comprises:
at least one releasable locking device to selectively lock the distal bearing plate relative to the proximal bearing plate in the first compact configuration;
wherein each releasable locking device has a first position that is engaged with both the distal bearing plate and the proximal bearing plate to maintain an initial distance therebetween; and
wherein the releasable locking device has a second position that is disengaged from one of the distal bearing plate and the proximal bearing plates to permit relative displacement of the proximal bearing plate away from the distal bearing plate to an increased distance therebetween.

18. The method of claim 17, wherein the releasable locking device has a hook pivotally mounted on one of the distal and proximal bearing plates and engaging an opposing one of the distal and proximal bearing plate.

19. A method of putting a ligament in tension, comprising:
resecting a joint surface of at least one of a tibia and a femur;
inserting a ligament-tensioning device into a space between the tibia and the femur, the device having at least one distal bearing plate and at least one proximal bearing plate, the device inserted into the space in a first compact configuration, and with at least one of the distal and proximal bearing plates disposed adjacent to the resected joint surface;
displacing the at least one proximal bearing plate and the at least one distal bearing plate away from one another so as to transition the device into a second expanded configuration to increase a space between the tibia and the femur; and
closing a joint capsule connecting the tibia and femur to enclose the bearing plates;
further comprising a drive element configured to drive the proximal bearing plate away from the distal bearing plate; and
wherein the drive element is configured such that it can be accommodated between the portions of the tibia and femur such that the joint capsule can be closed while the ligament-tensioning device is positioned in the joint capsule.

20. The method of claim 19, wherein the drive element is entirely accommodated within a space between the distal bearing plate and the proximal bearing plate.

21. The method of claim 19, wherein the drive element comprises a self-contained unit that does not require auxiliary energy to drive the proximal bearing plate away from the distal bearing plate.

22. A method of putting a ligament in tension, comprising:
resecting a joint surface of at least one of a tibia and a femur;
inserting a ligament-tensioning device into a space between the tibia and the femur, the device having at least one distal bearing plate and at least one proximal bearing plate, the device inserted into the space in a first compact configuration, and with at least one of the distal and proximal bearing plates disposed adjacent to the resected joint surface, the device having a displacer for displacing the proximal and distal bearing plates away from one another, wherein the displacer is accommodated within the space between the tibia and femur such that a joint capsule connecting the tibia and femur can be closed while the device including the displacer is positioned in the joint capsule;
wherein the device has at least one releasable locking device to selectively lock the distal bearing plate relative to the proximal bearing plate in the first compact configuration, each releasable locking device having a first position engaged with both the distal bearing plate and the proximal bearing plate to maintain an initial distance therebetween, and wherein the releasable locking device has a second position disengaged from one of the distal bearing plate and the proximal bearing plates to permit relative displacement of the proximal bearing plate away from the distal bearing plate to an increased distance therebetween to transition the device into the second expanded configuration;
transitioning the releasable locking device from the first position to the second position to permit relative displacement of the proximal bearing plate away from the distal bearing plate; and
displacing the proximal bearing plate and the distal bearing plate away from one another via the displacer and transitioning the device into the second expanded configuration to increase the space between the tibia and the femur; and
closing the joint capsule connecting the tibia and femur to enclose the device including the displacer entirely within the joint capsule.

23. The method of claim 22, wherein the releasable locking device has a hook pivotally mounted on one of the distal and proximal bearing plates and engaging an opposing one of the distal and proximal bearing plate in the first position.

24. The method of claim 22, wherein the displacer comprises a self-contained unit that does not require auxiliary energy to displace the proximal and distal bearing plates away from one another.

25. The method of claim 22, wherein the device further comprises:
at least one additional releasable locking device structured to selectively lock the distal bearing plate relative to the proximal bearing plate; the method further comprising:
engaging the additional releasable locking device with both the distal bearing plate and the proximal bearing plate to maintain an initial distance between the distal and proximal bearing plates; and
disengaging the additional releasable locking device from one of the distal bearing plate and the proximal bearing plate to permit relative displacement of the proximal bearing plates away from the distal bearing plate to an increased distance between the distal and proximal bearing plates.

26. The method of claim 25, wherein components of the ligament-tensioning device including the distal bearing plate, the proximal bearing plate, and the displacer are dimensioned such that they are entirely accommodated between portions of the tibia and femur.

27. The method of claim 22,
wherein the displacer is entirely accommodated within a space between the distal bearing plate and the proximal bearing plate.

* * * * *